United States Patent [19]
Pogue et al.

[11] Patent Number: 5,575,236
[45] Date of Patent: Nov. 19, 1996

[54] METHOD OF USING AN ANT HABITAT CONSTRUCTION

[76] Inventors: Lonnie C. Pogue, 1736 W. Montecito Way, San Diego, Calif. 92103; Brian Macowski, 2088 Montgomery, Apt. #N, Cardiff by the Sea, Calif. 92007

[21] Appl. No.: 388,383

[22] Filed: Feb. 14, 1995

[51] Int. Cl.[6] .................................................. A01K 67/033
[52] U.S. Cl. ........................... 119/6.5; 119/250; 119/416; D30/108
[58] Field of Search .............................. 119/6.5, 15, 246, 119/247, 248, 249, 250; D30/108; 220/23.2, 23.4; 449/6, 26; 40/152, 606

[56] References Cited

U.S. PATENT DOCUMENTS

| | | | |
|---|---|---|---|
| 1,810,745 | 6/1931 | Austin | 119/6.5 |
| 2,080,160 | 5/1937 | Austin | 119/6.5 |
| 2,174,305 | 9/1939 | Austin | 119/6.5 |
| 3,653,357 | 4/1972 | Sheidlower et al. | 119/6.5 |
| 3,687,110 | 8/1972 | Braunhut | 119/6.5 |
| 4,250,833 | 2/1981 | Waldon | 119/6.5 |
| 4,271,618 | 6/1981 | Lyman | 40/152 |
| 4,998,362 | 3/1991 | Stewart et al. | 40/152 |

*Primary Examiner*—Todd E. Manahan
*Attorney, Agent, or Firm*—Bernard L. Kleinke; Peter P. Scott

[57] ABSTRACT

An ant habitat construction bowed in shape in a convex manner between its side edges, and large pad devices help to provide mechanical stability. Upper and lower hollow hinge devices enable similar units to be connected together in an articulated manner and in communication with one another to facilitate ant travel between the units, and yet have enhanced stability.

3 Claims, 9 Drawing Sheets

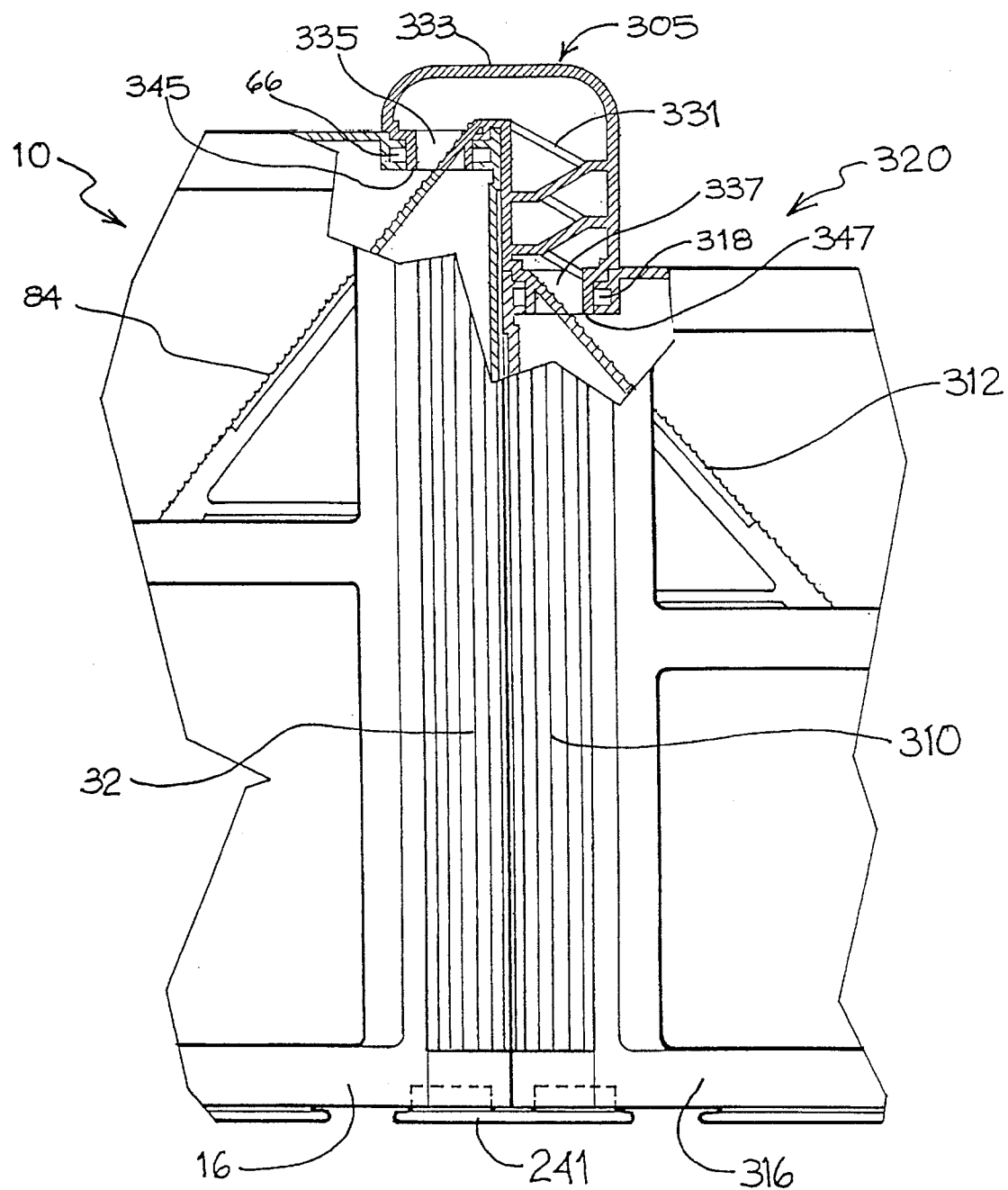

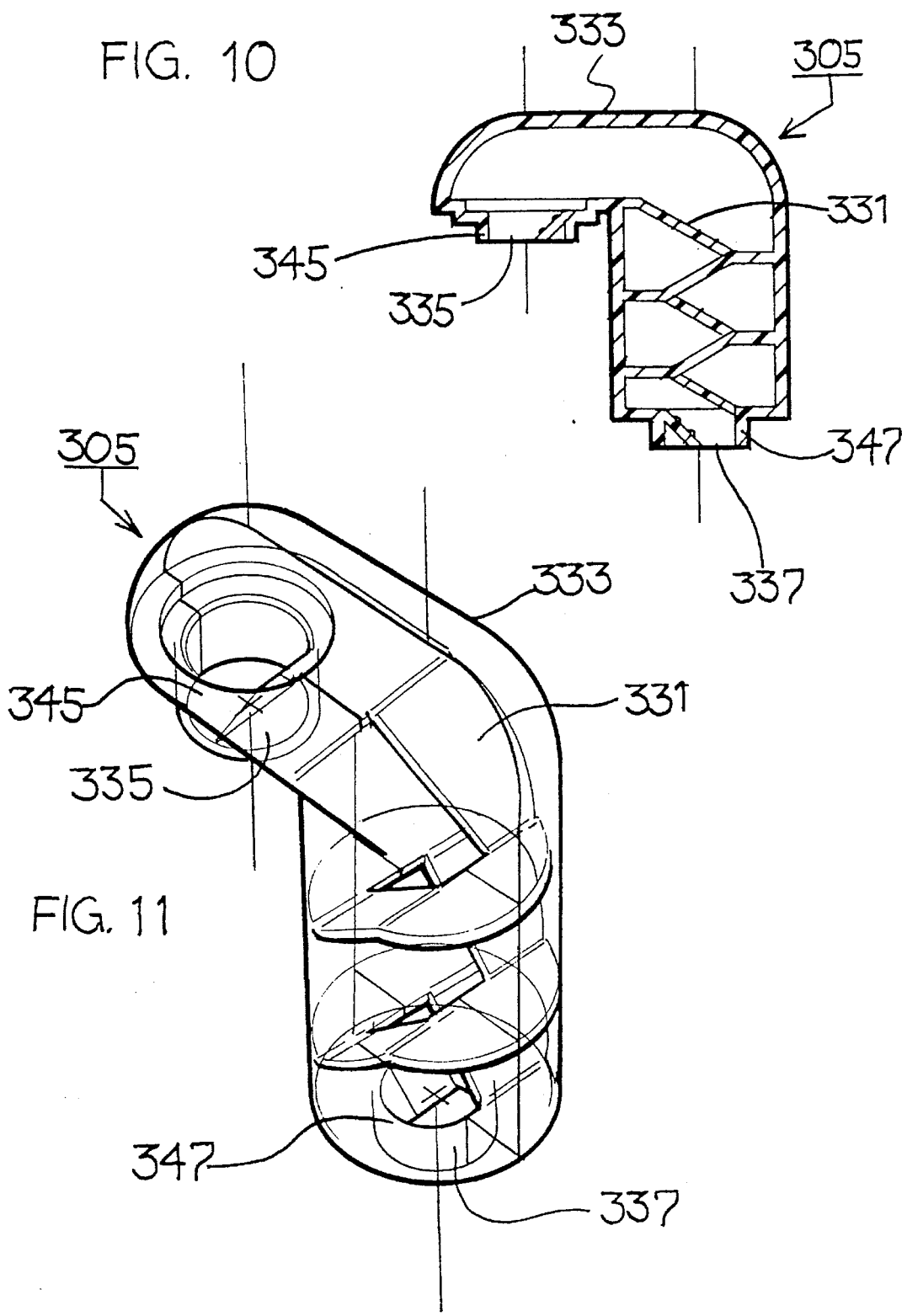

METHOD OF USING AN ANT HABITAT CONSTRUCTION

TECHNICAL FIELD

This invention relates generally to a habitat construction and a method of using it for containing and viewing insects, such as ants, and it more particularly relates to such a construction and method to achieve improved mechanical stability of the unit and greater versatility of use.

BACKGROUND ART

Ants are fascinating creatures. There are over 4,600 species of ants. Ants make their homes nearly everywhere, from beaches and mountains, to forests and deserts, and even the framework of houses.

Ants can do amazing things. They can dig great networks of tunnels, some as deep as fifteen feet underground. They can pick up and carry objects that are many times their own weight, and they can move at a speed that compares to a person running 65 miles per hour.

It is common for young people to capture, confine and observe ants within habitat structures commonly sold under the trademark ANT FARM®. The conventional structure is made of clear glass or plastic having a narrow and deep inner compartment partially filled with particulate material or soil. Ants are added and proceed to dig tunnels. The clear narrow container allows observation of the activities of the ants, both above and below the artificial ground.

The typical conventional ant habitat structure is tall and narrow in construction. Very often, the base of the ant habitat is also narrow, and such a construction can cause the structure to be easily tipped over inadvertently. Therefore, it would be highly desirable to have an ant habitat construction, which is more stable than the prior known units.

Conventional ant habitats allow for a connection between the habitat units by providing a flexible tubular tunnel from one interior compartment to another. When two such ant habitats are connected by a tunnel connector in this manner, the overall stability of the coupled complex is further compromised. In fact, such an assembly is more prone to inadvertent tipping over such as by striking either unit with an adequate force to cause both of the connected units to fall over, under the force of gravity. Therefore, it would be highly desirable to have a technique for interconnecting a pair of ant habitats in such a manner that would enhance the stability of the coupled assembly, and yet permit ants from one unit to travel freely between the units.

DISCLOSURE OF INVENTION

Therefore, the principal object of the present invention is to provide a new and improved ant habitat construction and method of using it to facilitate observation of the ants contained therein, and to increase the mechanical stability of the unit.

Another object of the present invention is to provide such a new and improved ant habitat construction and method to enable easy and convenient coupling to other similar ant habitat units, and to permit the ants to travel freely between the units.

Briefly, the above and further objects of the present invention are realized by providing an ant habitat construction bowed in shape in a convex manner between its side edges, and large pad devices help to provide mechanical stability. Upper and lower hollow hinge devices enable similar units to be connected together in an articulated manner and in communication with one another to facilitate ant travel between the units, and yet have enhanced stability.

BRIEF DESCRIPTION OF DRAWINGS

The above mentioned and other objects and features of this invention and the manner of attaining them will become apparent, and the invention itself will be best understood by reference to the following description of the embodiment of the invention in conjunction with the accompanying drawings, wherein:

FIG. 6 is a reduced scale plan view of the ant habitat mounted in wall mount unit;

FIG. 9 is an enlarged-scale fragmentary front elevational view of the two ant habitats of FIG. 8, illustrating the manner of interconnection between them;

FIG. 10 is an enlarged scale front elevational sectional view of an ant habitat connector tunnel used to connect two ant habitats of FIG. 8;

FIG. 11 is an enlarged scale pictorial view of an ant habitat connector tunnel of FIG. 10;

FIG. 12 is a reduced scale plan view of the ant habitat of FIG. 1, shown coupled to another habitat to form a W-shaped configuration in accordance with the present invention;

FIG. 13 is a reduced scale plan view of the ant habitat of FIG. 1, shown coupled to another habitat to form an S-shaped configuration in accordance with the present invention;

FIG. 14 is a reduced scale plan view of the ant habitat of FIG. 1, shown coupled to another habitat to form an elliptically shaped configuration in accordance with the present invention;

FIG. 15 is a reduced scale plan view of the ant habitat of FIG. 1, shown coupled to two other habitats and shown adapted to be mounted at a wall corner in accordance with the present invention; and FIG. 16 is a plan view of the ant habitat of FIG. 1, shown coupled to two other habitats to form a full circle configuration according to the invention.

BEST MODE FOR CARRYING OUT THE INVENTION

Figure 1:
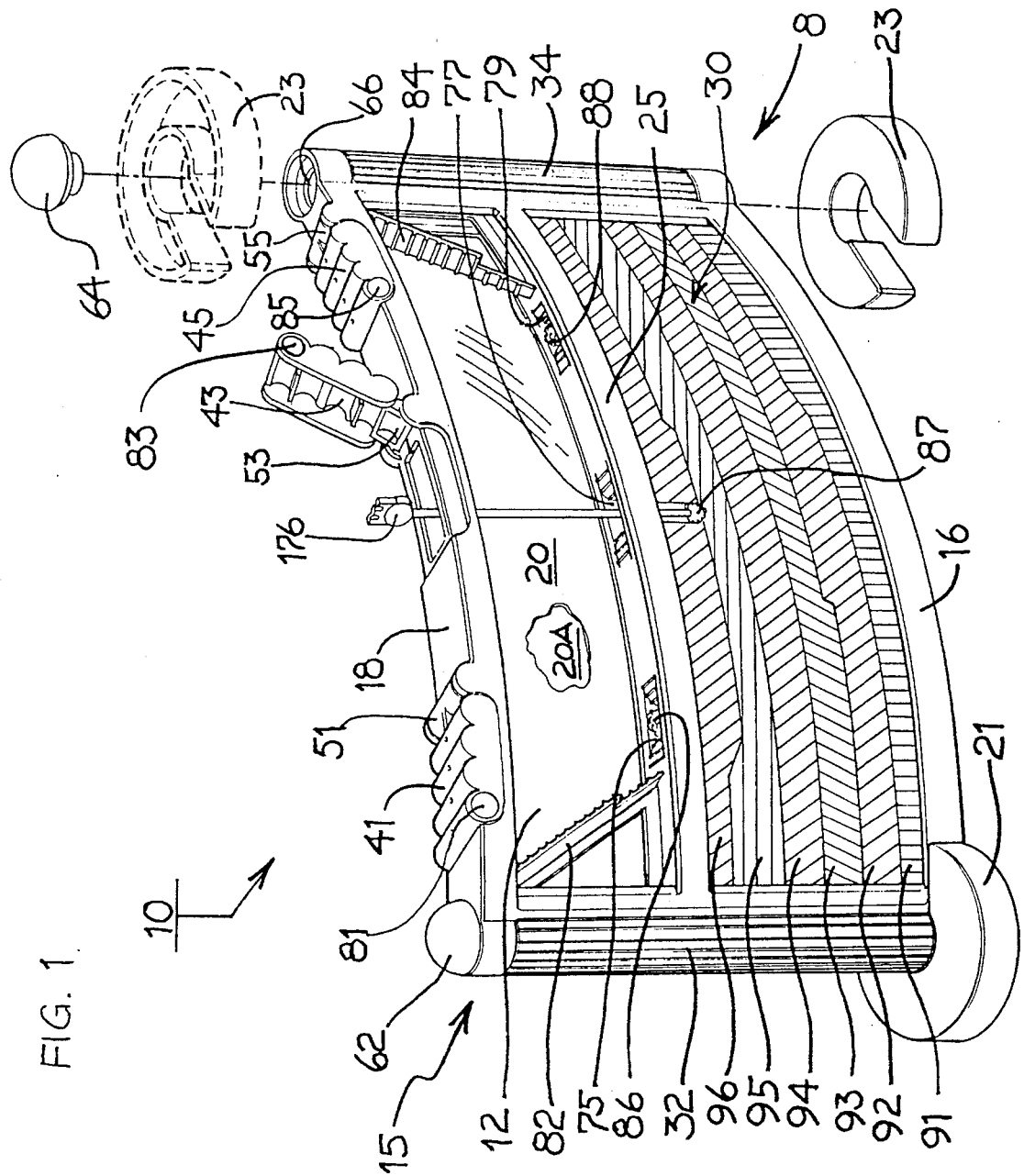
FIG. 1 is a partially exploded pictorial view of an ant habitat, which is constructed according to the present invention.
Figure 2:
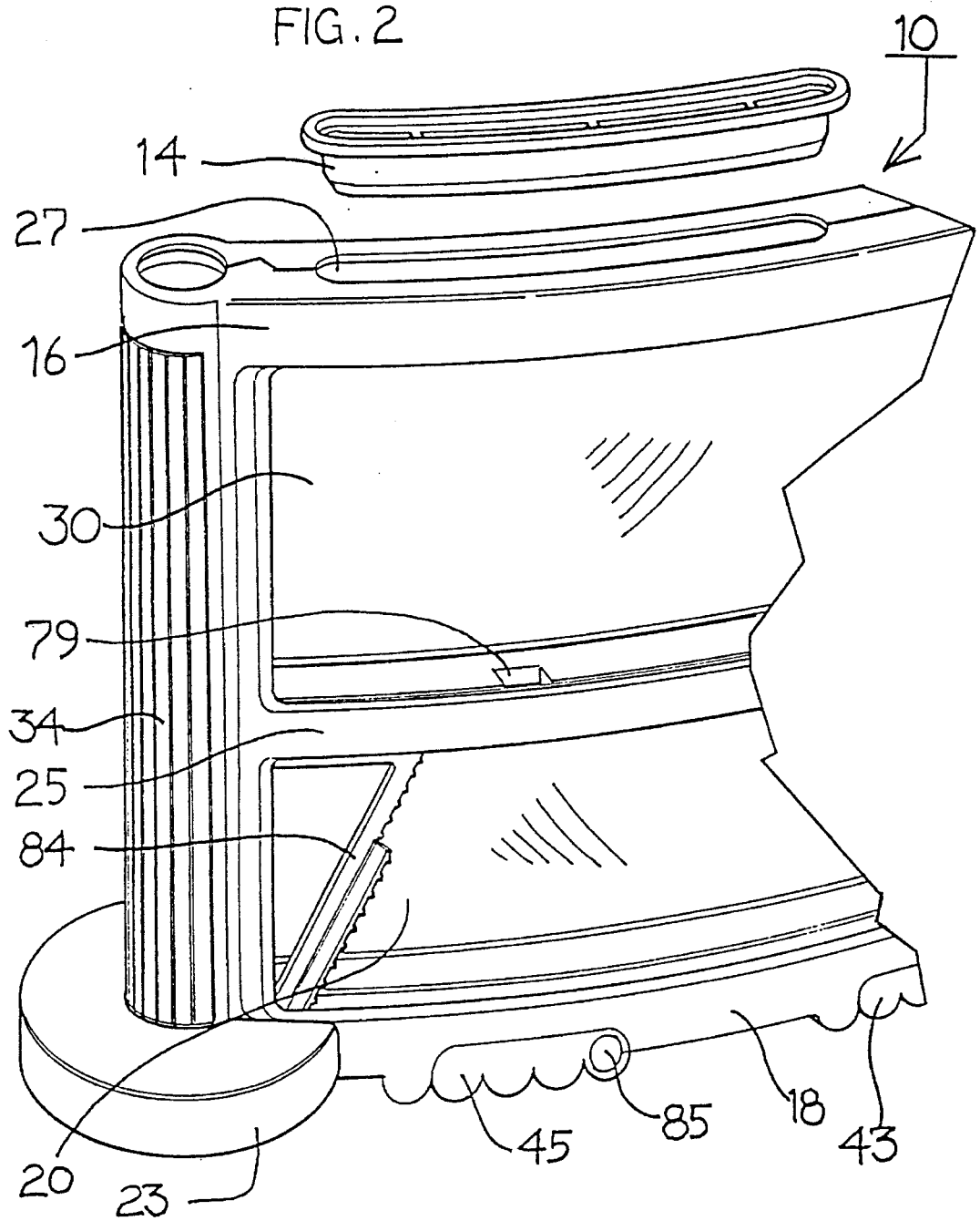
FIG. 2 is a partially exploded broken away enlarged pictorial view of an inverted ant habitat of FIG. 1, illustrating the manner of filling it.
Figure 3:
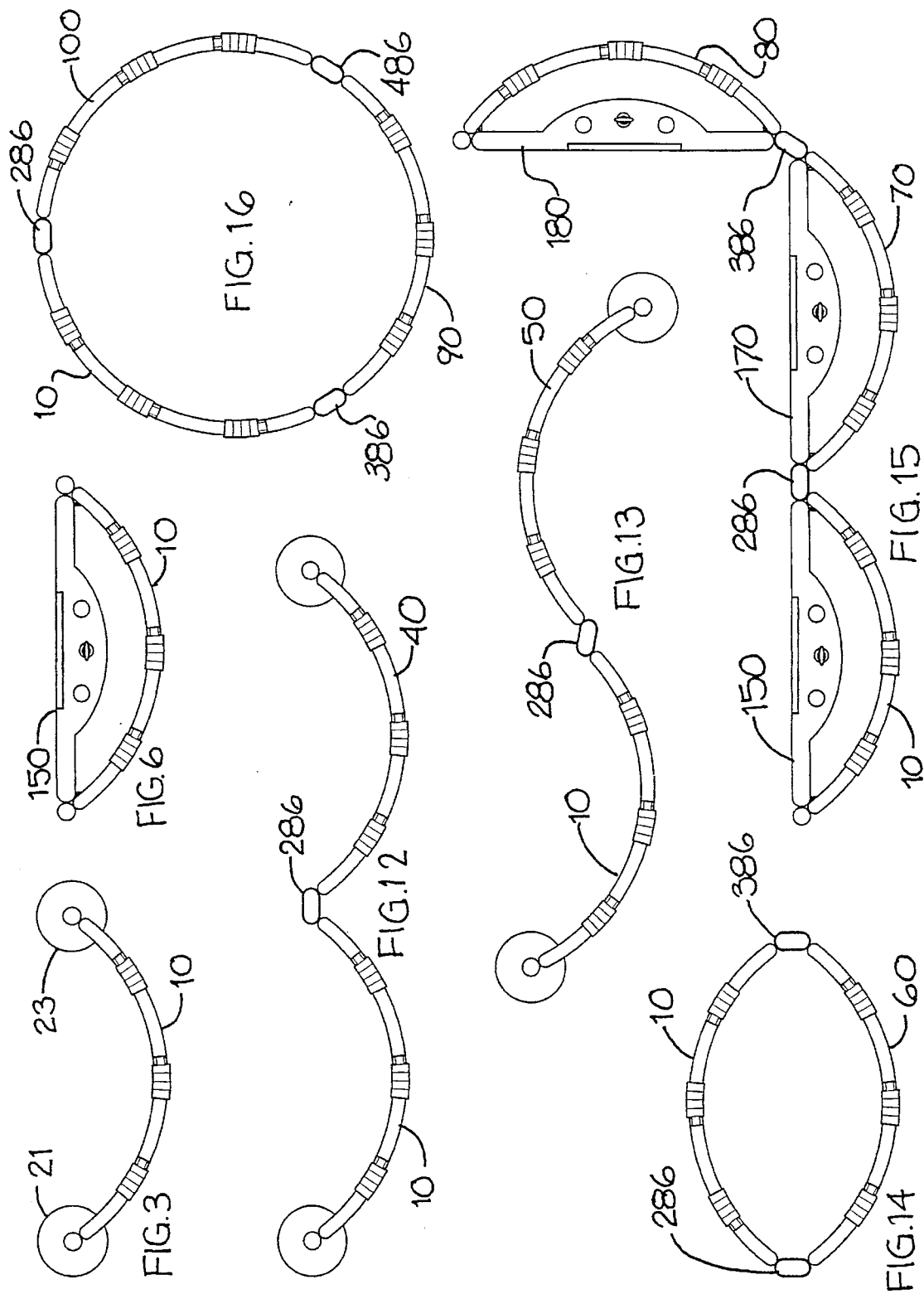
FIG. 3 is a plan view of the ant habitat of FIG. 1, illustrating it in a reduced scale.

Referring now to the drawings, and more particularly to FIGS. 1, 2 and 3 thereof, there is shown a new and improved ant habitat 10, which is constructed in accordance with the present invention. The habitat 10 is adapted to receive living insects or creatures, such as ants (not shown) to facilitate viewing their activities.

The ant habitat 10 generally includes a generally curved front plate or wall 12 and a parallel spaced apart curved rear plate or wall 12A. The plates are made from a translucent material such as clear transparent material, such as glass or plastic. The preferred material for this use is clear plastic.

The front and rear plates 12 and 12A, which serve as windows, help form a housing 8 mounted in an upright manner on the bottom base member 16. The housing 8 has a generally thin rectangular shape and is bowed in shape in a convex manner between its side edges to provide an aesthetically pleasing convex curved configuration. The housing 8 has at least one internal compartment for receiving and confining particulate materials.

The housing 8 has at least one transparent window for viewing the contents of the compartment.

A base member 16 at the bottom of the ant habitat unit 10 supports the unit from below. A pair of foot pads 21 and 23 are removably connected to the distal ends of the base member 16 when the ant habitat 10 is in the upright position as shown in FIG. 1. The large foot pads 21 and 23 help provide mechanical stability for the housing 8 to help prevent inadvertent tipping over of the housing. The foot pads 12 and 23 have a diameter D which is substantially equal to about one-third of the height H, of the housing 8. Whereas the housing 8 has a height H, the foot pads 21 and 23 have a diameter D such that H/D is equal to between about 3.5 and about 1.5, to enhance the stability of the ant habitat 10 and prevent the ant habitat 10 from tipping over when a force acting normal to the housing 8 is exerted upon the ant habitat 10. In the preferred embodiment of the invention, H/D is equal to about 2.5.

The two curved front and rear plates 12 and 12A, which serve as windows, are supported on the sides by column supports 32 and 34. The column supports are connected to the base member 16 at their bottom distal ends. The support columns 32 and 34 also support the top member 18.

The top member 18 includes at least one access door and up to three separate access doors such as 41, 43 and 45, as shown in FIG. 1. The access doors 41, 43 and 45 are movably connected to the top member 18 by hinges 51, 53 and 55. Access doors open and close to allow access into the upper interior chamber 20 of the ant habitat 10, for the purpose of adding ants, food, and water to the ant habitat 10.

Decorative dome-shaped caps 62 and 64 are removably connected to the top member 18, directly above support columns 32 and 34, respectively. When in place, the caps 62 and 64 fit snugly into complementary shaped apertures such as aperture 66, but are adapted to be removed to accommodate attachment of the foot pads 21 and 23 at the top member distal ends. The foot pads 21 and 23 are adapted to be attached at the top of the unit to enable the ant habitat 10 to rest on a supporting surface in an inverted manner, to permit the user to fill the unit at its underside with particulate material, as shown in FIG. 2. In this manner, the ant habitat 10 is stabilized during the filling operation. Furthermore, the decorative caps 62 and 64 are removed when connecting additional ant habitats to the ant habitat 10, as will be described hereinafter in greater detail below.

The ant habitat 10 is divided into two interior chambers, the upper interior chamber 20 and the lower interior chamber 30, by a horizontal frame member separator 25. Two ramps 82 and 84 lead from the upper surface of the horizontal frame member separator 25 to the upper corners of the upper inner chamber 20 and aperture 66. Ramps 82 and 84 provide the ants in the upper interior chamber 20 with access to other ant habitat upper interior chambers when two or more ant habitats are coupled as will be described in greater detail hereinafter.

The frame member separator 25 includes one or more surface apertures, such as surface aperture 75, 77 and 79, as shown in FIG. 1. These surface apertures provide the ants in the upper interior chamber 20 access to the particulate material filled lower interior chamber 30, so that the ants may dig a network of tunnels throughout the lower chamber 30.

In operation, the lower chamber 30 of the ant habitat 10 is filled with particulate material, preferably layers of different colored particulate material such as particulate material layers 91, 92, 93, 94, 95 and 96, as shown in FIG. 1. The preferred particulate materials include colored sand, fine gravel, vermiculite and pearlite.

During this filling process, the ant habitat 10 is inverted so that the underside of the base member 16 is exposed, as best shown in FIG. 2. One or more fill doors 14 are located in the base member 16, and when removed, provide access to the lower inner chamber 30 through opening 27, for filling the lower inner chamber 30 with particulate material. Horizontal frame member 25 and the cotton plugs 86, 87 and 88 retain the particulate material such that only the lower interior chamber 30 is filled.

Upon completion of the particulate material fill process, the ant habitat 10 is replaced in its upright position (FIG. 1) and the foot pads 21 and 23 are affixed to the base member. Decorative caps 62 and 64 are then placed in the apertures, such as aperture 66, shown in the top member 18 above the support columns 32 and 34.

Before adding ants to the ant habitat, at least one cotton plug 86, 87 or 88, should be cleared from one of the apertures 75, 77 or 79, respectively, and a tunnel started, to allow the ants access to the lower interior compartment 30 to facilitate the production of tunnels by the ants. This can be accomplished using the particulate material rake/tunnel starter implement 176. For example, access door 43 is opened. The blunt end of the tunnel starter 176 is extended into the upper interior compartment until it makes contact with cotton plug 87 located in aperture 77. The cotton plug is then forced downward into the particulate material layers 96 and 95, using the tunnel starter 176 and applying a downward force. The tunnel starter 176 is then removed and can be used to start other tunnels in the same manner, as desired.

Next, ants, food and water (not shown) may be added to the upper interior chamber 20 through one or more of the access doors 41, 43 and 45, hingedly connected to the top member 18. For example, access door 41, 43 or 45 may be lifted by a user (not shown) by grasping the access door at the slightly protruding circle 81, 83 or 85, respectively, and swinging the access door upwardly until partially or fully open.

FIG. 3 shows a plan view of the inventive ant habitat 10. The ant habitat 10 achieves exceptional stability by being curved and having large foot pads 21 and 23. These two features together help in preventing accidental tip over of the ant habitat 10.

The diameter of the foot pads 21 and 23 is substantial to prevent tipping over when a force acting normal to the ant habitat housing 15 is exerted. In this regard, foot pad diameter D relates to housing height H such that H/D is equal to between about 1.5 and 3.5. The preferred relationship of H to D is such that H/D is equal to about 2.5.

Figure 4:
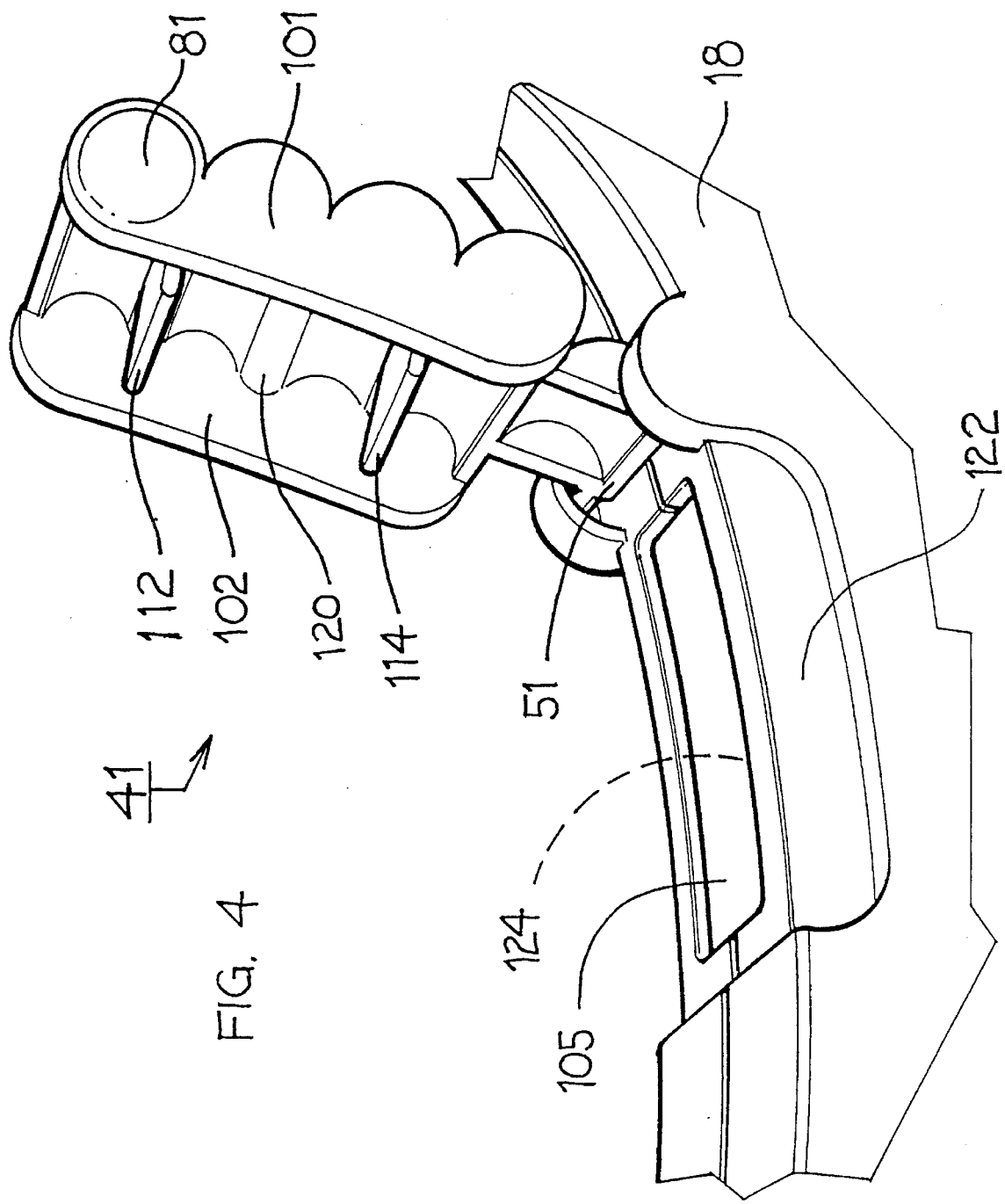
FIG. 4 is a greatly enlarged pictorial, partially broken away view of the upper access door disposed at the top of the ant habitat of FIG. 1, the door being illustrated in its opened position.

Considering now the access door 41 in greater detail with reference to FIG. 4, the access door 41 is shown in the open position. The access door 41 includes vertical side surfaces 101 and 102 and a horizontal top surface 120. The access door 41 is movably connected to the top member 18 of the ant habitat by a hinge 51. When in the open position, the opening 105 in the top member 18 is exposed and allows access to the interior of the ant habitat. When in the closed position, the access door 41 effectively seals off the interior chamber of the ant habitat. When closed, the access door 41 side surfaces 101 and 102 fit slidably into the recessed portions 122 and 124, respectively, in the top member. Furthermore, the top fins 112 and 114 protruding from the upper inner surface 120 fit snugly into the aperture 105 at the distal ends securing the access door 41 into place, in the closed position. In this regard, there is little or no possibility of ants escaping from the ant habitat inner chamber while the access doors are in their closed position.

To open the closed access door 41 and provide access into the ant habitat, a user grasps the access door 41 at the slightly protruding circle 81 located on the distal end of the access door 41 opposite the hinge 51 and lift.

Figure 5:
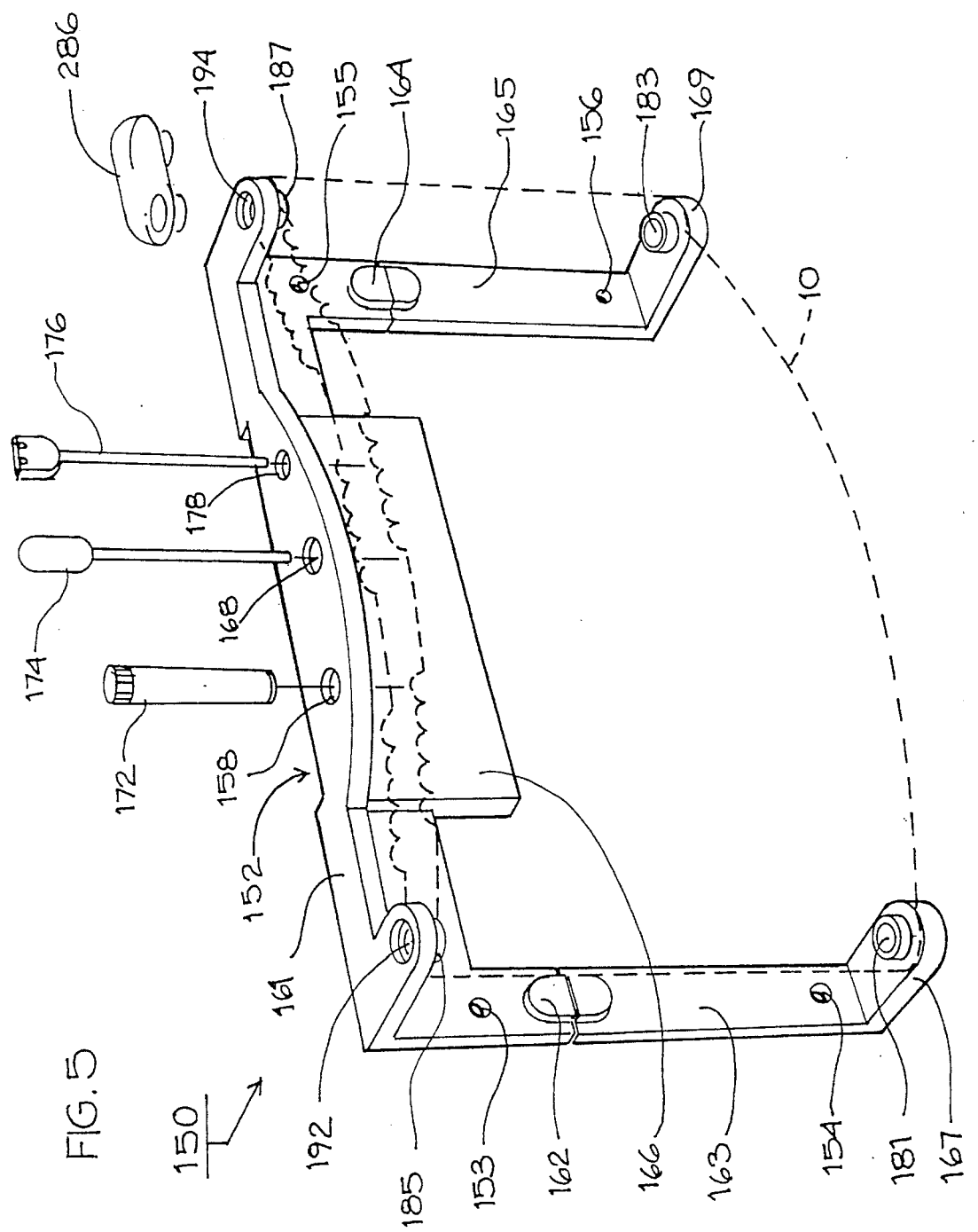
FIG. 5 is a partially exploded pictorial view of an ant habitat wall mount unit and accessories for use with the habitat of FIG. 1.

Considering now a novel apparatus for mounting the ant habitat 10, with reference to FIG. 5, there is shown a wall mount unit 150. The wall mount unit 150 enables a user to conveniently and easily mount an ant habitat on a wall or other flat surface. Additionally, the wall mount unit 150 provides convenient storage for ant habitat accessories and facilitates the coupling of two or more ant habitats when multiple wall mount units are placed adjacent to one another.

Considering now the wall mount unit 150 in greater detail with reference to FIG. 5, the wall mount unit includes a frame 152 having a plurality of spaced apart circular openings 153, 154, 155 and 156. These openings provide for affixing the wall mount unit 150 to a wall or other flat surface using threaded fasteners. The frame 152 consists of a top member 161, and two side members 163 and 165, integrally connected to two L-shaped lower members 167 and 169, respectively. The two side members 163 and 165 are removably attached to the top member 161 at connectors 162 and 164. In this way, the wall mount unit 150 will accommodate both large and small ant habitats by using long side members 163 and 165 or short side members (not shown) and attaching them at connectors 162 and 164.

The top member 161 has several apertures 158, 168 and 178 which allow the ant habitat accessories, that is, the ant vial 172, the water dropper 174 and the particulate material rake/tunnel starter 176, to be conveniently stored on the wall mount unit 150. Furthermore, a pocket 166 is molded into the rear portion of top member 161 of frame 152 to accommodate the ant habitat guide book (not shown), or some other literature, notes, etc.

In accordance with a wall mounting procedure, the wall mount unit 150 is first mounted on a wall (not shown) or other flat surface (not shown). Then, the ant habitat 10 is snapped into place on the wall mount unit 150 by placing the lower circular protrusions 181 and 183 located on lower L-shaped members 167 and 169, respectively, into complementary shaped recesses in the ant habitat (not shown). Next, by flexing downwardly the lower members 167 and 169, the top of the ant habitat can be secured by inserting the upper circular protrusions 185 and 187 into complementary shaped apertures in the ant habitat (not shown). Once mounted, channels 192 and 194, through the upper protrusions 185 and 187 on the top member 161 of the wall mount unit frame 152, allows communication between the inner chamber of the ant habitat and the outer environment. Thus, before ants are added to the inner chamber of the ant habitat, caps (not shown) should be placed upon the channels 192 and 194. In the event that another ant habitat is coupled to the mounted ant habitat, then channel connector 286 can be placed over one of the channels. In this regard, ants can freely travel between the two mounted ant habitats.

FIG. 6 shows a plan view of the inventive ant habitat being held by a wall mount unit 150.

Figure 7:
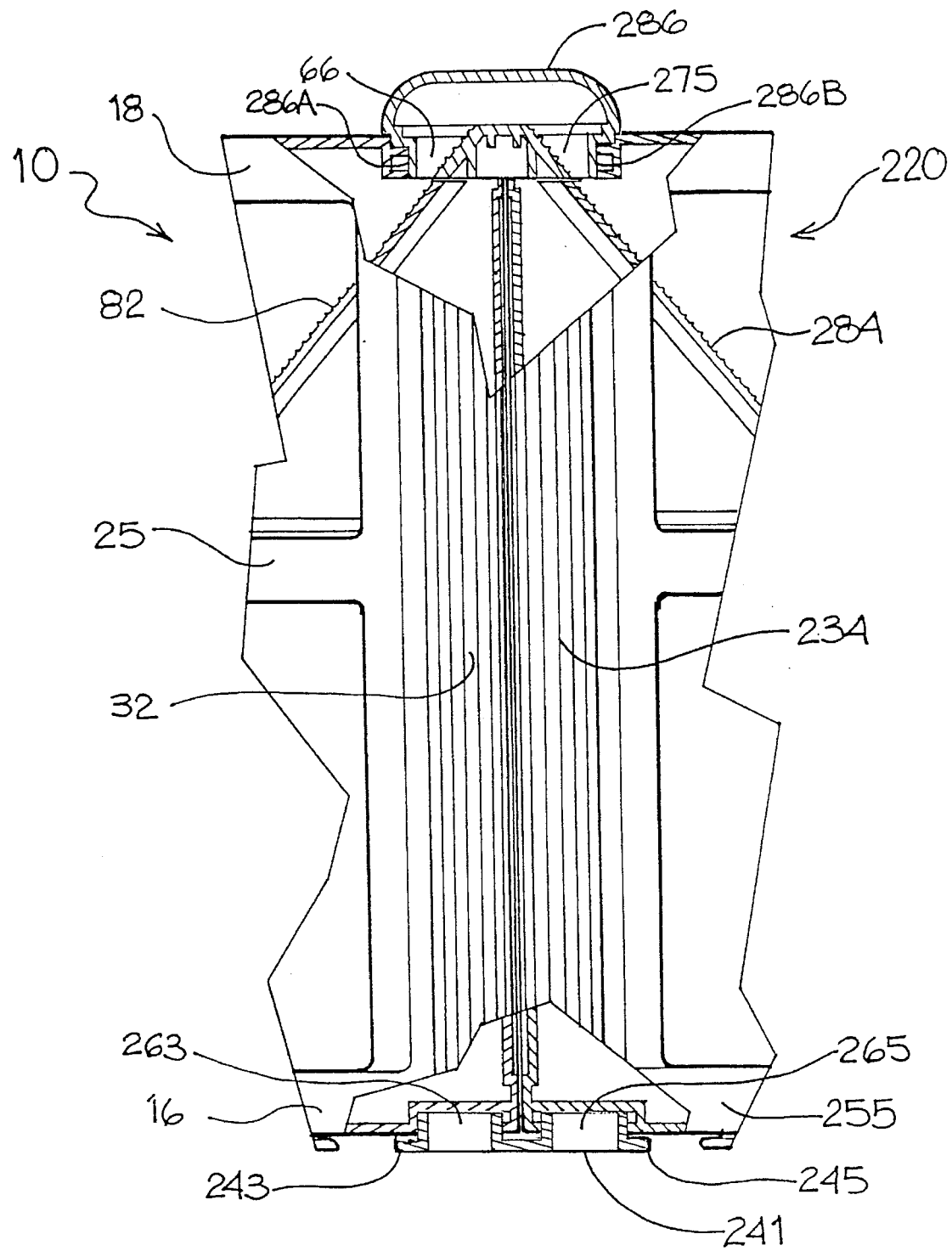
FIG. 7 is an enlarged, partially broken away, front elevational view of the habitat of FIG. 1, illustrating it connected to a similarly sized ant habitat in accordance with the present invention.

Considering now the technique of coupling two ant habitats, with reference to FIG. 7, there is shown two of the inventive ant habitats 10 and 220, coupled together to form an ant habitat construction assembly. Ant habitats 10 and 220 shown coupled in FIG. 7 are the same size ant habitats with respect to height. It should be understood that the inventive method for coupling ant habitats also allows for ant habitats of different heights to be coupled, as will be described hereinafter in greater detail for FIGS. 8–11, below.

In order to couple two ant habitats, the ant habitats 10 and 220 are placed adjacent to one another with the support columns 32 and 234 parallel. A bottom connector 241 is fastened to the base members 16 and 255 of the ant habitats 10 and 220, respectively. The bottom connector 241 is attached by firmly positioning the circular protrusions 243 and 245 into cup-shaped recessions 263 and 265 located in the base members of ant habitats 10 and 220, respectively, directly below the support columns 32 and 234.

To complete the coupling process, a U-shaped tubular channel cross-over connector 286 has reduced diameter end portions 286A and 286B snugly fitted into apertures 66 and 275 within ant habitats 10 and 220, respectively.

Figure 8:
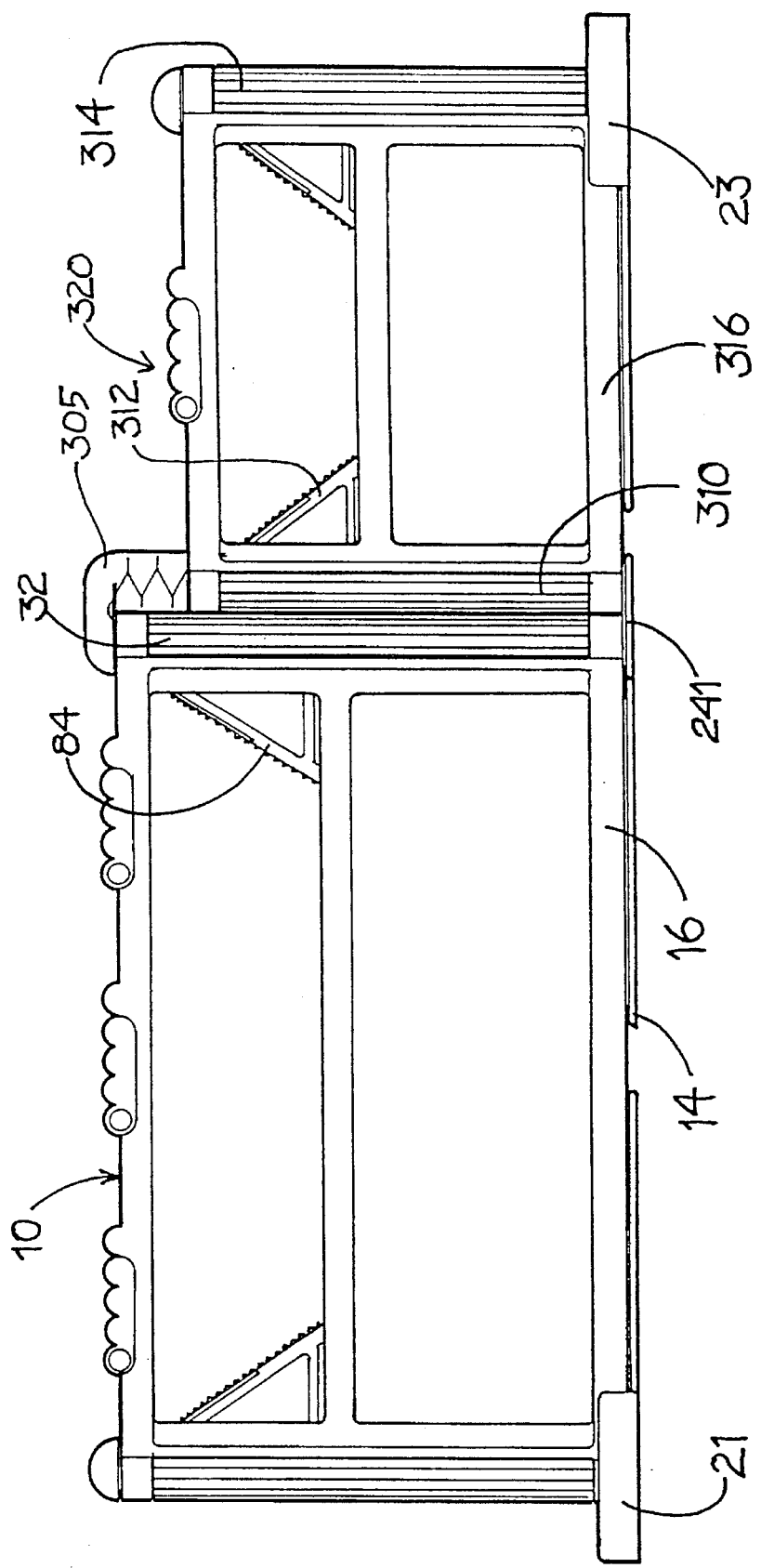
FIG. 8 is a reduced-scale front elevational view of the ant habitat of FIG. 1, illustrating it connected to a small sized ant habitat in accordance with the present invention.

Considering now the method of coupling two ant habitats, with reference to FIG. 8, there is shown two of the inventive ant habitats 10 and 320, coupled together. Ant habitats 10 and 320 are different sized ant habitats with respect to height and length.

In order to couple two ant habitats of differing sizes, the removable foot pad 23 on the lower support column 32 of larger ant habitat 10 is removed and placed on the lower portion of support column 314 of smaller ant habitat 320. Removable foot pad 21 remains in place on larger ant habitat 10. If any decorative dome caps (not shown) are present at the top of support column 32 on ant habitat 10 or support column 310 of smaller ant habitat 320, they must be removed. The two ant habitats 10 and 320 are then positioned such that support column 32 and support column 310 are adjacent to one another.

Next, a bottom connector 241 is fastened to the base members 16 and 316 of ant habitats 10 and 320, respectively. The final step in the coupling process is the fitting of the upper connector 305 into the apertures (not shown) at the top of the support column 32 and 310 on ant habitats 10 and 320, respectively.

Considering now the upper connector 305 used to couple two ant habitats of different sizes, in greater detail with reference to FIGS. 9–11, the upper connector 305 is generally hollow throughout its length and has an inner spiral rampway 331. The tubular connector 305 is generally U-shaped with one leg shorter than the other to accommodate the differing heights of the units. The connector 305 is generally circular in cross section throughout its length. The connector 305 serves both as a hinge to help connect the two units in an articulated manner, and a passageway for the ants by connecting the hollow interiors of the two units in communication with one another.

The upper connector 305 has a transparent plastic outer body 333 which defines two openings 335 and 337, and which permits the observation on the ants as they move between the units. The two openings 335 and 337 are surrounded by two reduced diameter protrusions 345 and 347, respectively, in the body 333 of the connector 305 to enable it to be connected with the respective apertures 66 and 318.

In operation, the protrusions 345 and 347 in the body 333 of the upper connector 305 fit snugly into apertures 66 and 318 located on the upper ends of support column 32 and 310 of ant habitats 10 and 320, respectively. When the upper connector 305 is in place, as best shown in FIG. 9, opening 335 allows access into the inner chamber of ant habitat 10, and opening 337 allows access into the inner chamber of ant habitat 320. Moreover, when upper connector 305 is snugly fitted into apertures 66 and 318 of ant habitats 10 and 320, respectively, then the inner spiral rampway 331 of the connector 305 aligns evenly with the ramps 84 and 312 of ant habitats 10 and 320, respectively. In this regard, the inner spiral rampway 331 facilitates the free travel of ants from one coupled ant habitat to the other. For example, an ant traveling from ant habitat 10 to ant habitat 320 would travel up ramp 84, through opening 335, along the spiral rampway 331, through opening 337, and down ramp 312 to end up within ant habitat 320.

The novel ant habitat and the inventive technique for coupling them together, enables the user to create interesting and creative ways of housing ants. Several of these interesting and creative ways of configuring two or more ant habitats into ant habitat construction assemblies is illustrated in FIGS. 12–16.

FIG. 12 shows two ant habitats 10 and 40 coupled together with connector 286 in a W-shaped configuration. It should be understood that while connector 286 has been used here, if ant habitats 10 and 40 were of differing sizes, then connector 305 may be used instead of connector 286.

FIG. 13 shows two ant habitats 10 and 50 coupled together with connector 286, in a generally S-shaped configuration.

FIG. 14 shows two ant habitats 10 and 60 coupled together by two connectors 286 and 386 in a free standing elliptical shaped configuration. This back-to-back closed loop arrangement of the ant habitats impart a great deal of stability to the coupled units and practically eliminates the possibility of accidental tip over.

FIG. 15 shows three ant habitats 10, 70 and 80 mounted on three wall mount units 150, 170 and 180, respectively. Ant habitat 80, mounted on wall mount unit 180 has been positioned to be at a right angle relative to ant habitat 70 mounted on wall mount unit 170, by pivoting at connector 386. In this regard, multiple wall mount units may be employed to mount multiple ant habitats at a corner section of a wall.

FIG. 16 shows three ant habitats 10, 90 and 100 coupled together using three connectors 286, 386 and 486, to form a free standing circular configuration. It should be understood that a greater number of ant habitats can be coupled together to form a free standing circular configuration. This circular arrangement provides greatly enhanced stability to the multiple ant habitat unit and the possibility of accidental tip over is virtually eliminated.

While particular embodiments of the present invention have been disclosed, it is to be understood that various different modifications are possible and are contemplated within the true spirit and scope of the appended claims. There is no intention, therefore, of limitations to the exact abstract or disclosure herein presented.

What is claimed is:

1. A method for using an ant habitat having a base means, a housing mounted in an upright manner on said base means and having a generally thin rectangular shape and being bowed in shape in a convex manner between its side edges to provide an aesthetically pleasing convex curved configuration, said housing having at least one internal compartment for receiving and confining particulate materials, said housing having at least one transparent window for viewing the contents of the compartment, said housing having an access opening therein for receiving the particulate materials, an access door means removably connected to the housing for sealing over the access opening, and said base means including large foot pad means, having a front portion and a rear portion, connected to the bottom of the housing for helping provide mechanical stability for the housing to help prevent inadvertent tipping over of the housing, said foot pad means having a dimension extending between the front and rear portions thereof being substantially equal to about one-third of the height of the housing, the method comprising the steps of:

inverting the ant habitat and having it rest on a supporting surface standing upside down;

removing a lower access cover to expose a lower access opening;

filling a lower interior compartment with particulate material by pouring the particulate material through said exposed lower access opening;

replacing said lower access cover to retain the particulate material within said lower interior compartment;

inverting the ant habitat to position it in an upright manner;

opening a hingedly connected upper access door to expose an upper access opening;

starting a tunnel;

adding burrowing insects to an upper interior compartment through said upper access opening;

closing said upper access door to confine the burrowing insects within the interior compartment; and wherein said step of inverting the ant habitat and having it rest on a supporting surface standing upside down includes attaching removable foot pads to that portion of the ant habitat contacting the supporting surface to enhance stability of the ant habitat during the filling operation.

2. A method for using an ant habitat having a base means, a housing mounted in an upright manner on said base means and having a generally thin rectangular shape and being bowed in shape in a convex manner between its side edges to provide an aesthetically pleasing convex curved configuration, said housing having at least one internal compartment for receiving and confining particulate materials, said housing having at least one transparent window for viewing the contents of the compartment, said housing having an access opening therein for receiving the particulate materials, an access door means removably connected to the housing for sealing over the access opening, and said base means including large foot pad means, having a front portion and a rear portion, connected to the bottom of the housing for helping provide mechanical stability for the housing to help prevent inadvertent tipping over of the housing, said foot pad means having a dimension extending between the front and rear portions thereof being substantially equal to about one-third of the height of the housing, the method comprising the steps of:

inverting the ant habitat and having it rest on a supporting surface standing upside down;

removing a lower access cover to expose a lower access opening;

filling a lower interior compartment with particulate material by pouring the particulate material through said exposed lower access opening;

replacing said lower access cover to retain the particulate material within said lower interior compartment;

inverting the ant habitat to position it in an upright manner;

opening a hingedly connected upper access door to expose an upper access opening;

starting a tunnel;

adding burrowing insects to an upper interior compartment through said upper access opening;

closing said upper access door to confine the burrowing insects within the interior compartment; and wherein said step of inverting the ant habitat to position it in an upright manner includes attaching removable foot pads to the lower portion of the ant habitat to enhance stability of the ant habitat to help prevent accidental tip over while the ant habitat is in use.

3. A method for using an ant habitat having a base means, a housing mounted in an upright manner on said base means and having a generally thin rectangular shape and being bowed in shape in a convex manner between its side edges to provide an aesthetically pleasing convex curved configuration, said housing having at least one internal compartment for receiving and confining particulate materials, said housing having at least one transparent window for viewing the contents of the compartment, said housing having an access opening therein for receiving the particulate materials, an access door means removably connected to the housing for sealing over the access opening, and said base means including large foot pad means, having a front portion and a rear portion, connected to the bottom of the housing for helping provide mechanical stability for the housing to help prevent inadvertent tipping over of the housing, said foot pad means having a dimension extending between the front and rear portions thereof being substantially equal to about one-third of the height of the housing, the method comprising the steps of:

inverting the ant habitat and having it rest on a supporting surface standing upside down;

removing a lower access cover to expose a lower access opening;

filling a lower interior compartment with particulate material by pouring the particulate material through said exposed lower access opening;

replacing said lower access cover to retain the particulate material within said lower interior compartment;

inverting the ant habitat to position it in an upright manner;

opening a hingedly connected upper access door to expose an upper access opening;

starting a tunnel;

adding burrowing insects to an upper interior compartment through said upper access opening;

closing said upper access door to confine the burrowing insects within the interior compartment;

wherein said step of starting a tunnel includes extending a tunnel starter implement through said upper access opening and into a cotton plug located within an interior compartment aperture;

pushing said cotton plug out of said aperture downwardly into the particulate material about one inch to clear the cotton plug from the aperture and help to begin the tunnel for the burrowing insects; and removing the tunnel starter from the interior compartment.

\* \* \* \* \*